(12) United States Patent
Summers et al.

(10) Patent No.: US 6,750,042 B2
(45) Date of Patent: Jun. 15, 2004

(54) METAL BINDING PROTEINS, RECOMBINANT HOST CELLS AND METHODS

(75) Inventors: Anne O. Summers, Athens, GA (US); Jonathan J. Caguiat, Ypsilanti, MI (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/977,137

(22) Filed: Oct. 12, 2001

(65) Prior Publication Data

US 2003/0104524 A1 Jun. 5, 2003

Related U.S. Application Data

(60) Provisional application No. 60/240,465, filed on Oct. 12, 2000.

(51) Int. Cl.$^7$ .............................. C12N 5/00; C12N 5/10; C12N 15/00
(52) U.S. Cl. ................... 435/69.1; 435/419; 435/320.1; 536/23.1
(58) Field of Search ............................ 435/69.1, 320.1, 435/419; 536/23.1

(56) References Cited

U.S. PATENT DOCUMENTS

| 5,506,121 A | 4/1996 | Skerra et al. ............... 435/69.7 |
| 5,972,656 A | 10/1999 | Lopez et al. ............... 435/69.3 |

FOREIGN PATENT DOCUMENTS

EP          0 585 652 A2    9/1994

OTHER PUBLICATIONS

Boulanger, Y. et al., "Model for mammalian metallothionein structure"(Mar. 1983) Proc. Natl. Acad. Sci. USA 80:1501–1505.
Brennan, R.G. and Matthews, B.W., "The Helix–Turn–Helix DNA Binding Motif" (Feb. 5, 1989) J. Biol. Chem. 264(4):1903–1906.
Caguiat, J.J. et al., "Cd(II)–Responsive and Constitutive Mutants Implicate A Novel Domain in MerR"(Jun. 1999)J. Bacteriol. 181(11):3462–3471.
Caguiat, J.J. and Summers, A.O., "Single Residue Changes Confer an Enhanced Response by MerR to Cd(II)" Abstracts of the General Meeting of the American Society for Microbiology (1998) 98p278.
Comess, K.L. et al., "Construction of a Synthetic Gene for the Metalloregulatory Protein MerR and Analysis of Regionally Mutated Proteins for Transcriptional Regulation" (1994) Biochemistry 33(14):4175–4786.
Engst, S. and Miller S. M., "Alternative Routes for Entry of $HgX_2$ into the Active Site of Mercuric Ion Reductase Depend on the Natureof the X Ligands" (Mar. 1999) Biochemistry 38(12):3519–3529.

Furey, W.F. et al., "Crystal Structure of Cd,Zn Metallothionein"(1986) Science 231:704–708.
GenBank, Accession No. P07044 (Apr. 1, 1988).
Godwin, H.A. and Berg, J.M., "A Fluorescent Zinc Probe Based on Metal–Induced Peptide Folding" (1996) J. Am. Chem. Sco. 118(27):6514–6515.
Helman, J.D. et al., "The MerR Metalloregulatory Protein Binds Mercuric Ion as a Tricoordinate, Metal–Bridged Dimer" (1990) Science 247:946–948.
Heltzel, A. et al., "Activator–Dependent Preinduction Binding of 0–70 RNA Polymerase at Metal–Regulated mer Promoter" (1990) Biochemistry 29:9572–9584.
Kulkarni, R.D. and Summers, A.O., "Architecture of RNA polymerase–MerR–Hg(II) complexes as the mer operator–promoter region as revealed by protein–protein crosslinking." (1998) Abstracts of the General Meeting of the American Society for Microbiology 98p278.
Livrelli, V. et al. "In Vivo DNA–Protein Interactions at the Divergent MErcury Resistance (mer) Promoters" (Feb. 1993) J. Biol. Chem. 268(4):2623–2631.
Miller, S.M. et al. "Communication between the Active Sites in Dimeric Mercuric Ion Reductase: An Alternating Sites Hypothesis for Catalysis" (1991)Biochemistry 30(10):2600–2612.
Miller, S.M. et al., "Two–electron Reduced Mercuric Reductase Binds Hg(II) to the Active Site Dithiol but Does Not Catalyze Hg(II) Reduction"(Jun. 1986) J. of Biol. Chem. 261(18):8081–8084.
Moore, M.J. et al., "C–Terminal Cysteines of Tn501 Mercuirc Ion Reductase" (1992) Biochemistry 31 (6):1677–1685.
O'Halloran, T.V., "Transition Metals in Control of Gene Expression" (Aug. 1993) Science 261:715–725.

(List continued on next page.)

Primary Examiner—Amy J. Nelson
Assistant Examiner—Medina A. Ibrahim
(74) Attorney, Agent, or Firm—Greenlee Winner and Sullivan PC

(57) ABSTRACT

The present disclosure provides artificial heavy metal binding proteins termed chelons by the inventors. These chelons bind cadmium and/or mercuric ions with relatively high affinity. Also disclosed are coding sequences, recombinant DNA molecules and recombinant host cells comprising those recombinant DNA molecules for expression of the chelon proteins. In the recombinant host cells or transgenic plants, the chelons can be used to bind heavy metals taken up from contaminated soil, groundwater or irrigation water and to concentrate and sequester those ions. Recombinant enteric bacteria can be used within the gastrointestinal tracts of animals or humans exposed to toxic metal ions such as mercury and/or cadmium, where the chelon recombinantly expressed in chosen in accordance with the ion to be rededicated. Alternatively, the chelons can be immobilized to solid supports to bind and concentrate heavy metals from a contaminated aqueous medium including biological fluids.

7 Claims, 5 Drawing Sheets

OTHER PUBLICATIONS

Ralston, D.M. et al., "Ultrasensitivity and heavy–metal selctivity of the allosterically modulated MerR transcription Complex" (May 1990)Proc. Natl. Acad. Sci. USA 87:3846–3850.

Ross, W. et al., "Genetic Analysis of Transcriptional Activation and Repression in the Tn21 mer Operon"(Jul. 1989) J. Bacteriol. 171:4009–4018.

Santos, R.A. et al., "Solid–State $^{199}$Hg and $^{113}$Cd NMR Studies of Mercury–and Cadmium–Thiolate Complexes. Spectroscopic Models for [Hg(Scys)$_n$] Centers in the Bacterial Mercury Resistance Protei"(1991) J. Am. Chem. Soc. 113(2):469–474.

Barineau, P. et al. (1984) "The DNA Sequence of the Mercury Resistnace Operon og The INC–F–11 Plasmid NR–1"; *J. of Moleularand Appled Genetics*2(6):601–620.

Bontidean, I. et al. (Apr. 2000) "Bacterial metal–resistance proteins and their use in biosensors fro the detection of bioavailable heavy metals"; *J. OF Inorganic Biochem.*79(1–4):225–229.

Chang, J–S et al., ((Oct. 1998) "Repeated fed–batch operations for microbial detoxification of mercury using wild–type and recombinant mercury–resistant bacteria", *J. of Biotech.* 64(2–3):219–230.

SEQUENCE LISTING

```
<160> NUMBER OF SEQ ID NOS: 18
<210> SEQ ID NO 1
<211> LENGTH: 435
<212> TYPE: DNA
<213> ORGANISM: Shigella flexneri, Tn21 of  Plasmid R100

<400> SEQUENCE: 1
atggaaaata  atttggaaaa  cctgaccatt  ggcgttttg   ccaaggcggc  cggggtcaac     60
gtggagacaa  tccgcttcta  tcagcgcaag  ggcctgtttgc  gggaaccgga  caagccttac    120
ggcagcatcc  gccgctatgg  ggaggcggac  gtggttcggg  tgaaattcgt  gaaatcggca    180
cagcggctgg  ggttcagtct  ggacgagatt  gccgagctgt  tgcggctcga  cgatggcacc    240
cactgcgagg  aggccagcag  cctggccgaa  cacaagctca  aggacgtgcg  cgagaagatg    300
gccgacttgg  cgcgcatgga  aaccgtgctg  tctgaactcg  tgtgcgcctg  ccatgcacga    360
```

-continued

```
aagggaatg tttcctgccc gttgatcgcg tcactacagg gcgaagcagg cctggcaagg    420
tcagctatgc cttag                                                    435
```

<210> SEQ ID NO 2
<211> LENGTH: 144
<212> TYPE: PRT
<213> ORGANISM: Shigella flexneri, Tn21 of Plasmid R100

<400> SEQUENCE: 2

```
Met Glu Asn Asn Leu Glu Asn Leu Thr Ile Gly Val Phe Ala Lys Ala
 1               5                  10                  15

Ala Gly Val Asn Val Glu Thr Ile Arg Phe Tyr Gln Arg Lys Gly Leu
                20                  25                  30

Leu Arg Glu Pro Asp Lys Pro Tyr Gly Ser Ile Arg Arg Tyr Gly Glu
            35                  40                  45

Ala Asp Val Val Arg Val Lys Phe Val Lys Ser Ala Gln Arg Leu Gly
        50                  55                  60

Phe Ser Leu Asp Glu Ile Ala Glu Leu Leu Arg Leu Asp Asp Gly Thr
 65                  70                  75                  80

His Cys Glu Glu Ala Ser Ser Leu Ala Glu His Lys Leu Lys Asp Val
                 85                  90                  95

Arg Glu Lys Met Ala Asp Leu Ala Arg Met Glu Thr Val Leu Ser Glu
            100                 105                 110

Leu Val Cys Ala Cys His Ala Arg Lys Gly Asn Val Ser Cys Pro Leu
        115                 120                 125

Ile Ala Ser Leu Gln Gly Glu Ala Gly Leu Ala Arg Ser Ala Met Pro
130                 135                 140
```

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: chelon

<400> SEQUENCE: 3

```
atgacacact gcgaggaggc cagcagcctg gccgaacaca agctcaagga cgtgcgcgag    60
aagatggccg acttggcgcg catggaaacc gtgctgtctg aactcgtgtg cgcctgccat   120
gcacgaaagg ggaatgtttc ctgcccgttg atcgcgtcac tacagggatc ctcaggcacc   180
cactgcgagg aggccagcag cctggccgaa cacaagctca aggacgtgcg cgagaagatg   240
gccgacttgg cgcgcatgga aaccgtgctg tctgaactcg tgtgcgcctg ccatgcacga   300 aagggaatg tttcctgccc g                                              321
```

<210> SEQ ID NO 4
<211> LENGTH: 117
<212> TYPE: PRT
<213> ORGANISM: Artificial Sequence
<220> FEATURE:
<223> OTHER INFORMATION: Description of Artificial Sequence: chelon

<400> SEQUENCE: 4

```
Met Thr His Cys Glu Glu Ala Ser Ser Leu Ala Glu His Lys Leu Lys
 1               5                  10                  15

Asp Val Arg Glu Lys Met Ala Asp Leu Ala Arg Met Glu Thr Val Leu
                20                  25                  30

Ser Glu Leu Val Cys Ala Cys His Ala Arg Lys Gly Asn Val Ser Cys
```

```
                 35                  40                  45
Pro Leu Ile Ala Ser Leu Gln Gly Ser Ser Gly Thr His Cys Glu Glu
         50                  55                  60

Ala Ser Ser Leu Ala Glu His Lys Leu Lys Asp Val Arg Glu Lys Met
 65                  70                  75                  80

Ala Asp Leu Ala Arg Met Glu Thr Val Leu Ser Glu Leu Val Cys Ala
                 85                  90                  95

Cys His Ala Arg Lys Gly Asn Val Ser Cys Pro Ser Ala Trp Ser His
                100                 105                 110

Pro Gln Phe Glu Lys
        115

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence:  chelon

<400> SEQUENCE: 5

Met Thr His Cys Glu Glu Val Ser Ser Leu Ala Glu His Lys Leu Lys
  1               5                  10                  15

Asp Val Arg Glu Lys Met Ala Asp Leu Ala Arg Met Glu Thr Val Leu
                 20                  25                  30

Ser Glu Leu Val Cys Ala Cys His Ala Arg Lys Gly Asn Val Ser Cys
             35                  40                  45

Pro Leu Ile Ala Ser Leu Gln Gly Ser Ser Gly Thr His Cys Glu Glu
         50                  55                  60

Val Ser Ser Leu Ala Glu His Lys Leu Lys Asp Val Arg Glu Lys Met
 65                  70                  75                  80

Ala Asp Leu Ala Arg Met Glu Thr Val Leu Ser Glu Leu Val Cys Ala
                 85                  90                  95

Cys His Ala Arg Lys Gly Asn Val Ser Cys Pro Ser Ala Trp Ser His
                100                 105                 110

Pro Gln Phe Glu Lys
        115

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence:  chelon

<400> SEQUENCE: 6

Met Thr His Cys Glu Glu Ala Ser Ser Leu Val Glu His Lys Leu Lys
  1               5                  10                  15

Asp Val Arg Glu Lys Thr Met Ala Asp Leu Ala Arg Met Glu Thr Val
                 20                  25                  30

Leu Ser Glu Leu Val Cys Ala Cys His Ala Arg Lys Gly Asn Val Ser
             35                  40                  45

Cys Pro Leu Ile Ala Ser Leu Gln Gly Ser Ser Gly Thr His Cys Glu
         50                  55                  60

Glu Ala Ser Ser Leu Val Glu His Lys Leu Lys Asp Val Arg Glu Lys
 65                  70                  75                  80

Met Ala Asp Leu Ala Arg Met Glu Thr Val Leu Ser Glu Leu Val Cys
                 85                  90                  95

Ala Cys His Ala Arg Lys Gly Asn Val Ser Cys Pro Ser Ala Trp Ser
```

```
                    100                 105                 110

His Pro Gln Phe Glu Lys
            115

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence:  chelon

<400> SEQUENCE: 7

Met Thr His Cys Glu Glu Ala Ser Ser Leu Ala Glu His Lys Leu Lys
  1               5                  10                  15

Asp Val Arg Glu Thr Met Ala Asp Leu Ala Arg Met Glu Thr Val Leu
                 20                  25                  30

Ser Glu Leu Val Cys Ala Cys His Ala Arg Lys Gly Asn Val Ser Cys
             35                  40                  45

Pro Leu Ile Ala Ser Leu Gln Gly Ser Ser Gly Thr His Cys Glu Glu
         50                  55                  60

Ala Ser Ser Leu Ala Glu His Lys Leu Lys Asp Val Arg Glu Thr Met
 65                  70                  75                  80

Ala Asp Leu Ala Arg Met Glu Thr Val Leu Ser Glu Leu Val Cys Ala
                 85                  90                  95

Cys His Ala Arg Lys Gly Asn Val Ser Cys Pro Ser Ala Trp Ser His
            100                 105                 110

Pro Gln Phe Glu Lys
            115

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence:  chelon

<400> SEQUENCE: 8

Met Thr His Cys Glu Glu Ala Ser Ser Leu Ala Glu His Lys Leu Lys
  1               5                  10                  15

Asp Val Arg Glu Gln Met Ala Asp Leu Ala Arg Met Glu Thr Val Leu
                 20                  25                  30

Ser Glu Leu Val Cys Ala Cys His Ala Arg Lys Gly Asn Val Ser Cys
             35                  40                  45

Pro Leu Ile Ala Ser Leu Gln Gly Ser Ser Gly Thr His Cys Glu Glu
         50                  55                  60

Ala Ser Ser Leu Ala Glu His Lys Leu Lys Asp Val Arg Glu Gln Met
 65                  70                  75                  80

Ala Asp Leu Ala Arg Met Glu Thr Val Leu Ser Glu Leu Val Cys Ala
                 85                  90                  95

Cys His Ala Arg Lys Gly Asn Val Ser Cys Pro Ser Ala Trp Ser His
            100                 105                 110

Pro Gln Phe Glu Lys
            115

<210> SEQ ID NO 9
<211> LENGTH: 117
<212> TYPE: PRT
<213> ORGANISM: Artificial Sequence
<220> FEATURE:
```

<223> OTHER INFORMATION: Description of Artificial Sequence: chelon

<400> SEQUENCE: 9

```
Met Thr His Cys Glu Glu Ala Ser Ser Leu Ala Glu His Lys Leu Lys
 1               5                  10                  15
Asp Val Arg Glu Lys Met Ala Asp Leu Ala Arg Val Glu Thr Val Leu
            20                  25                  30
Ser Glu Leu Val Cys Ala Cys His Ala Arg Lys Gly Asn Val Ser Cys
        35                  40                  45
Pro Leu Ile Ala Ser Leu Gln Gly Ser Ser Gly Thr His Cys Glu Glu
    50                  55                  60
Ala Ser Ser Leu Ala Glu His Lys Leu Lys Asp Val Arg Glu Lys Met
65                  70                  75                  80
Ala Asp Leu Ala Arg Val Glu Thr Val Leu Ser Glu Leu Val Cys Ala
                85                  90                  95
Cys His Ala Arg Lys Gly Asn Val Ser Cys Pro Ser Ala Trp Ser His
            100                 105                 110
Pro Gln Phe Glu Lys
        115
```

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: chelon

<400> SEQUENCE: 10

```
Met Thr His Cys Glu Glu Ala Ser Ser Leu Ala Glu His Lys Leu Lys
 1               5                  10                  15
Asp Val Arg Glu Lys Met Ala Asp Leu Ala Arg Ile Glu Thr Val Leu
            20                  25                  30
Ser Glu Leu Val Cys Ala Cys His Ala Arg Lys Gly Asn Val Ser Cys
        35                  40                  45
Pro Leu Ile Ala Ser Leu Gln Gly Ser Ser Gly Thr His Cys Glu Glu
    50                  55                  60
Ala Ser Ser Leu Ala Glu His Lys Leu Lys Asp Val Arg Glu Lys Met
65                  70                  75                  80
Ala Asp Leu Ala Arg Ile Glu Thr Val Leu Ser Glu Leu Val Cys Ala
                85                  90                  95
Cys His Ala Arg Lys Gly Asn Val Ser Cys Pro Ser Ala Trp Ser His
            100                 105                 110
Pro Gln Phe Glu Lys
        115
```

<210> SEQ ID NO 11
<211> LENGTH: 117
<212> TYPE: PRT
<213> ORGANISM: Artificial Sequence
<220> FEATURE:
<223> OTHER INFORMATION: Description of Artificial Sequence: chelon

<400> SEQUENCE: 11

```
Met Thr His Cys Glu Glu Ala Ser Ser Leu Ala Glu His Lys Leu Lys
 1               5                  10                  15
Asp Val Arg Glu Lys Met Ala Asp Leu Ala Arg Met Glu Thr Val Leu
            20                  25                  30
Ser Glu Leu Val Cys Ala Cys His Ala Arg Lys Gly Asn Val Pro Cys
```

35                  40                  45
Pro Leu Ile Ala Ser Leu Gln Gly Ser Ser Gly Thr His Cys Glu Glu
        50                  55                  60

Ala Ser Ser Leu Ala Glu His Lys Leu Lys Asp Val Arg Glu Lys Met
 65                  70                  75                  80

Ala Asp Leu Ala Arg Met Glu Thr Val Leu Ser Glu Leu Val Cys Ala
                 85                  90                  95

Cys His Ala Arg Lys Gly Asn Val Pro Cys Pro Ser Ala Trp Ser His
                100                 105                 110

Pro Gln Phe Glu Lys
        115

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: chelon

<400> SEQUENCE: 12

Met Thr His Cys Glu Glu Ala Ser Ser Leu Ala Glu His Lys Leu Lys
  1               5                  10                  15

Asp Val Arg Glu Lys Met Ala Asp Leu Ala Arg Met Glu Thr Val Leu
                 20                  25                  30

Ser Glu Leu Val Cys Ala Cys His Ala Arg Lys Gly Asn Val Ser Cys
            35                  40                  45

Pro Leu Ile Ala Leu Leu Gln Gly Ser Ser Gly Thr His Cys Glu Glu
        50                  55                  60

Ala Ser Ser Leu Ala Glu His Lys Leu Lys Asp Val Arg Glu Lys Met
 65                  70                  75                  80

Ala Asp Leu Ala Arg Met Glu Thr Val Leu Ser Glu Leu Val Cys Ala
                 85                  90                  95

Cys His Ala Arg Lys Gly Asn Val Ser Cys Pro Ser Ala Trp Ser His
                100                 105                 110

Pro Gln Phe Glu Lys
        115

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 13
tgcggcggtc tcaaatgaca cactgcgagg agg                               33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 14
gcctgaggat ccctgtagtg acgcgatcaa cgg                               33

<210> SEQ ID NO 15
<211> LENGTH: 30
<212> TYPE: DNA

```
<213> ORGANISM: Artificial Sequence
<220> FEATURE:
<223> OTHER INFORMATION: Description of Artificial Sequence:  primer

<400> SEQUENCE: 15
ctacagggat cctcaggcac ccactgcgag                                          30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:  primer

<400> SEQUENCE: 16
ctgtagggtc tcggcgctcg ggcaggaaac att                                      33

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence:  sequence
      encoding chelon

<400> SEQUENCE: 17
atgacacact gcgaggaggc cagcagcctg gccgaacaca agctcaagga cgtgcgcgag         60
aagatggccg acttggcgcg catggaaacc gtgctgtctg aactcgtgtg cgcctgccat        120
gcacgaaagg ggaatgtttc ctgcccgttg atcgcgtcac tacagggatc ctcaggcacc        180
cactgcgagg aggccagcag cctggccgaa cacaagctca aggacgtgcg cgagaagatg        240
gccgacttgg cgcgcatgga aaccgtgctg tctgaactcg tgtgcgcctg ccatgcacga        300
aaggggaatg tttcctgccc gagcgcttgg agccacccgc agttcgaaaa ataa              354

<210> SEQ ID NO 18
<211> LENGTH: 509
<212> TYPE: DNA
<213> ORGANISM: Artificial Sequence
<220> FEATURE:
<223> OTHER INFORMATION: Description of Artificial Sequence:sequence
      encoding chelon flanked by sequences derived from
      plasmid

<400> SEQUENCE: 18
ccatcgaatg gccagatgat taattcctaa ttttttgttga cactatcatt gatagagtta        60
ttttaccact ccctatcagt gatagagaaa agtgaaatga atagttcgta caaaaatcta       120
gataacgagg gcaaaaaatg acacactgcg aggaggccag cagcctggcc gaacacaagc       180
tcaaggacgt gcgcgagaag atggccgact tggcgcgcat ggaaaccgtg ctgtctgaac       240
tcgtgtgcgc ctgccatgca cgaaagggga atgtttcctg cccgttgatc gcgtcactac       300
agggatcctc aggcacccac tgcgaggagg ccagcagcct ggccgaacac aagctcaagg       360
acgtgcgcga gaagatggcc gacttggcgc gcatggaaac cgtgctgtct gaactcgtgt       420
gcgcctgcca tgcacgaaag gggaatgttt cctgcccgag cgcttggagc cacccgcagt       480
tcgaaaaata taagcttga cctgtgaag                                          509
```

METAL BINDING PROTEINS, RECOMBINANT HOST CELLS AND METHODS

CROSS REFERENCE TO RELATED APPLICATIONS

This application claims benefit of U.S. Provisional Application No. 60/240,465, filed Oct. 12, 2000, which is incorporated herein to the extent that there is no inconsistency with the present disclosure.

ACKNOWLEDGMENT OF FEDERAL RESEARCH SUPPORT

This invention was made, at least in part, with funding from the United States Department of Energy (Grant No. DE-FG02-99ER62865). Accordingly, the United States Government has certain rights in this invention.

BACKGROUND OF THE INVENTION

The field of the present invention is the area of molecular biology, in particular as related to a metal-binding protein produced through recombinant DNA technology.

One of the best-characterized mercury resistance (mer) operons is located on transposon Tn21 from the *Shigella flexneri* IncFII plasmid R100. This operon consists of five structural genes—merT, merP, merC, merA, and merD—and a regulatory gene, merR (FIG. 1). MerT, MerP, and MerC are involved in the transport of Hg(II) into the cell. MerA is a cytosolic, NADPH-dependent, flavin adenine dinucleotide-containing oxidoreductase which reduces Hg(II) to Hg(0). The merR gene is transcribed in the direction opposite from that of the structural genes. Its product, MerR, represses expression of the merTPCAD genes in the absence of Hg(II), activates their expression in the presence of Hg(II), and represses its own expression in the presence or absence of Hg(II). MerD plays a minor role in regulation, possibly as an antagonist of MerR, which reestablishes repression of merTPCAD once Hg(II) has teen reduced to Hg(0).

Extensive genetic and biochemical data indicate that the protein contains three domains [Ross; et al. (1989) *J. Bacteriol.* 171:4009–4018; Shewchuk et al. (1989) *Biochemistry* 28:2340–2344; Summers, A. O. (1992) *J. Bacteriol.* 174:3097–3101]: a helix-turn-helix DNA-binding domain from L10 to R29 [Brennan et al. (1989) *J. Biol. Chem.* 264:1903–1906; Livrelli et al. (1993) *J. Biol. Chem.* 268:2623–2631]; a "coupling" domain from K30 to H81 which may convey the status of the Hg(II) binding site to the DNA binding site [Comess et al. (1994) *Biochemistry* 33:4175–4186; Helmann et al. (1990) *Science* 247:946–948]; and a long helical region from C82 to C117 which constitutes both the dimer interface and, with the loop containing C126, the Hg(II)-binding domain [Zeng et al. (1998) *Biochemistry* 37:15885–15895].

The MerR homodimer binds Hg(II) by using the thiols of three conserved cysteines: cysteine 82 (C82) from one monomer and cysteines 117 and 126 (C117 and C126) from the other monomer. These ligands form a novel planar tricoordinate complex with Hg(II) [Helman et al. (1990) supra; O'Halloran, T. V. (1993) *Science* 261:715–725; Utschig et al. (1995) *Science* 26:380–385; Wright et al. (1990) *J. Am. Chem. Soc.* 112:2434–2435]. Upon binding Hg(II), MerR undergoes a conformational change that leads to an underwinding of the $P_r$ region and thereby enables RNA polymerase to form an open complex. Curiously, although the MerR homodimer contains two potential Hg(II) binding sites, the purified protein binds only one Hg(II) per dimer. Moreover, although the two other group 12 metals, Zn(II) and Cd(II), also form stable complexes with protein thiols [Boulanger et al. (1983) *Proc. Natl. Acad. Sci. USA* 80:1501–1505; Furey et al. (1986) *Science* 231:704–708; Santos et al. (1991) *J. Am. Chem. Soc.* 113:469–474; Utschig et al. (1993) *Methods Enzymol.* 226:71–97], purified MerR binds Hg(II) preferentially even in the presence of a 1,000-fold excess of Cd(II) or Zn(II) [Shewchuk et al. (1989) *Biochemistry* 28:2331–2339] and also requires 100- to 1,000-fold higher concentrations of these metals for transcriptional activation [Ralston et al. (1990) *Proc. Natl. Acad. Sci. USA* 87:3846–3850.

Although several studies have described mutants altered in either repression or activation, no genetic study of merR has explicitly addressed the basis of its metal specificity prior to Caguiat et al. (1999) *J. Bacteriol.* 181:3462–3471. Caguiat et al. report variants of MerR with an altered response to a metal; the properties and locations of these mutations shed light on the basis for metal-provoked activation by MerR. That also led those authors to examine the possible occurrence of similar secondary-structure elements in other members of the MerR family, and our findings in the latter regard indicate conservation of a structural domain in a subset of this family.

There is a long felt need in the art for compositions and methods useful in the remediation of materials contaminated with heavy metal ions, especially mercury and cadmium. The present invention provides artificial metal binding proteins, coding sequences, recombinant DNA molecules, recombinant host cells and methods for production of the artificial metal binding proteins.

SUMMARY OF THE INVENTION

The present invention provides DNA sequences encoding artificial metal binding proteins, which are termed chelons herein, and DNA sequences encoding the mercury binding protein MerR (derived from Tn21), vectors comprising those sequences operably linked to promoters functional in particular host cells of choice, recombinant host cells expressing the chelon proteins or MerR protein and methods of producing the chelon proteins and MerR protein recombinantly. Host cells include, but are not limited to, bacterial cells (e.g., *Escherichia coli, Bacillus subtilis*, Pseudomonas species, etc.), yeast cells (e.g., *Sacciaromyces cerevisiae* or *Pichia pastoris*), fungi (e.g., Aspergillus species, *Trichoderma reesei*), plant cells (e.g., Arabidopsis, tobacco, petunia, Populus species, Salix species, among others) and animal cells such as CHO cells or avian cells.

The present invention further provides chelon proteins which bind heavy metal ions, including but not limited to divalent cadmium and mercury ions, as well as cobalt, copper, lead, nickel and zinc cations, with relatively high affinity. The amino acid sequence of a mercury-specific chelon is disclosed in Table 1D, and the nucleotide sequence encoding it is present in Table 1C. Additional chelons which bind both mercury and cadmium ions with high affinity are disclosed in Table 2. The chelon proteins can be within cells or on the surfaces of the cells in which they were produced, for example, for use in methods of concentrating heavy metal ions from a contaminated aqueous environment, or waste stream, or the chelon proteins can be immobilized onto a solid support for use in removal of heavy metal ions from a contaminated aqueous medium. The MerR protein can also be produced for in situ metal ion binding, or it can be purified and immobilized to a support material.

Also within the scope of the present invention are methods of removing heavy metal ions from contaminated aqueous solutions, waste streams or contaminated environments, for example, using immobilized chelon or MerR proteins, immobilized cells containing the MerR or chelon proteins or using whole plants to take up, sequester and concentrate the heavy metal ions from contaminated soil, ground water, hydroponic solutions, irrigation water or waste streams. Selective expression of the MerR or chelon proteins in above-ground plant parts (such as stems and leaves) allows the harvesting of the plant material in which the heavy metal ions have been sequestered and concentrated. Those plant parts can then be disposed of or processed in an environmentally appropriate manner.

DETAILED DESCRIPTION OF THE INVENTION

Figure 1D:
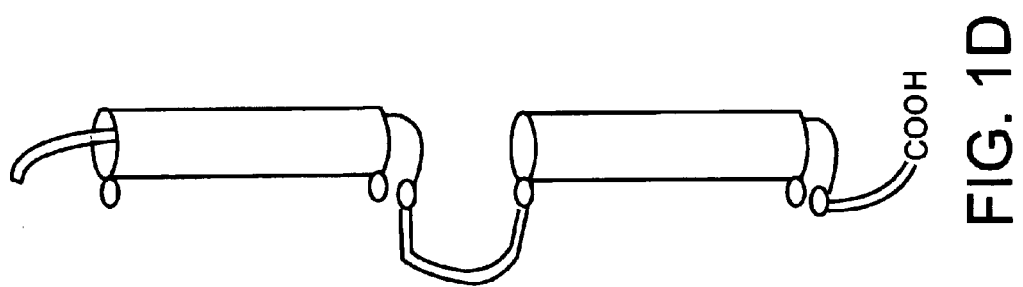
FIGS. 1D–1E illustrate the chelon protein with its tandem metal binding domains. The shapes are as in FIG. 1A except that the hatched curves represent the nonwild-type linker residues which allow association of the coiled-coils and stabilize the protein.
Figure 1C:
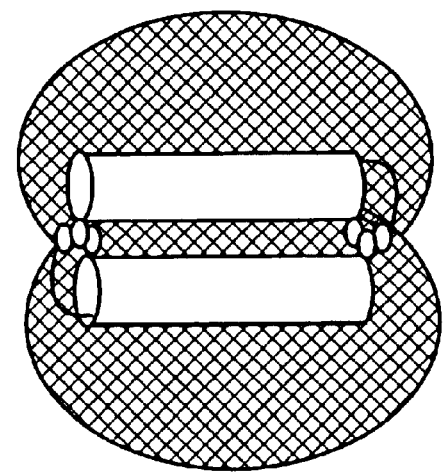
FIGS. 1A–1C illustrate the full length wild-type MerR protein, as the monomer, the dimeric coiled-coil metal binding domain and the mercury-bound dimeric metal binding domain, respectively. In each, the tube represents the coiled-coil region, the small open spheres represent cysteine residues, the hatched curve is the short loop regions, the large cross-hatched circles represent all other regions of the protein, and the small black sphere represents bound mercuric ion. Dimer in solution binds one Hg ion because of the conformational change.
Figure 1E:
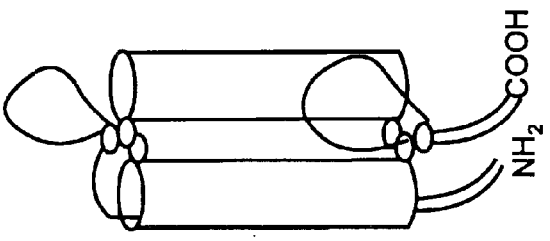
Figure 1B:
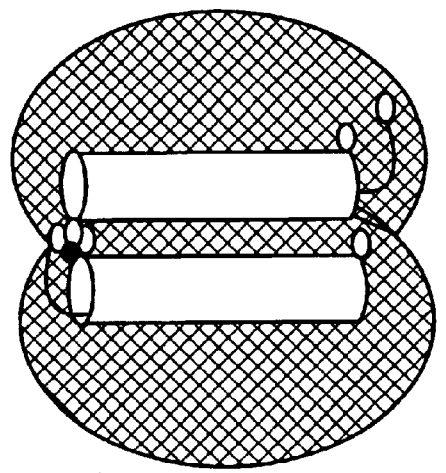
Figure 1A:
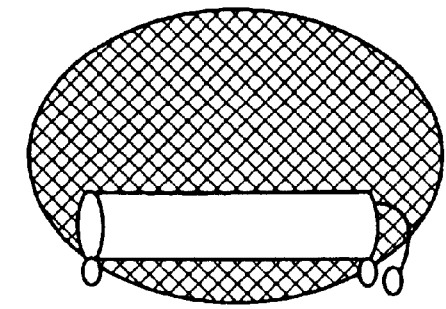

In order to provide a clear and consistent understanding of the specification and claims, including the scope to be given to such terms, the following definitions are provided.

A coding sequence is the part of a gene or nucleic acid molecule which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

Downstream of means on the 3' side of any site in DNA or RNA, and upstream of means on the 5' side of a site in DNA or RNA.

Expression refers to the transcription of a coding sequence into structural RNA (rRNA, tRNA) or messenger RNA (mRNA) and subsequent translation of a mRNA into a protein.

An amino acid sequence that is functionally equivalent to a chelon or MerR protein of the present invention is an amino acid sequence that has been modified by single or multiple amino acid substitutions, by addition and/or deletion of amino acids, or where one or more amino acids have been chemically modified, but which nevertheless retains the heavy metal binding activity of a chelon (or MerR protein) of the present invention. Functionally equivalent nucleotide sequences are those that encode polypeptides having substantially the same biological activity.

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

Isolated means altered by the hand of man from the natural state. If an isolated composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A linker region is an amino acid sequence that operably links two functional or structural domains of a protein, for example, between two metal binding domains of a chelon.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'–5'-phosphodiester bonds.

Two DNA sequences are operably linked if the nature of the linkage does not interfere with the ability of the sequences to effect their normal functions relative to each other. For instance, a promoter region is operably linked to a coding sequence if the promoter is capable of effecting transcription of that coding sequence in a particular host cell of choice.

A polypeptide is a linear polymer of amino acids linked by peptide bonds.

A promoter is a cis-acting DNA sequence, generally 80–120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into its cloning site or its polylinker).

Transformation means the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

The chelon specifically embodied by the present invention is an artificial protein comprising at least two metal binding domains derived from the MerR protein of the Tn21 mer (mercury resistance) operon. In the presence of mercuric ions, the MerR protein binds mercuric ions and serves as a positive regulator of the mercury resistance operon. An isolated metal binding domain polypeptide has been described [Zeng et al. (1998) *Biochemistry* 37:15885–15895]. See also Caguiat et al. (1990 *J. Bacteriol.* 181:3462–3471, for further discussion of heavy metal binding by the MerR protein and cadmium-binding variants.

The present work provides the first demonstration that an independent sub-domain of a naturally occurring protein can be incorporated in a heavy metal sequestration protein which binds thiophilic metal ions with high affinity. Previously described metal binding proteins are those which bind divalent "beneficial" metal ions, e.g., nickel, copper and zinc. Generally for those proteins, the affinities and specificities for heavy metals are lower, although some forms of metallothionein bind divalent cadmium ions. The previously known metal binding proteins are subject to having the metal ligand competed off by naturally occurring thiols such as glutathione and cysteine. The relatively low affinities reflect the physiological roles of these proteins in serving as chaperones for the metal ions en route to the active sites of enzymes or structural sites of DNA binding proteins. The intact MerR protein and its metal binding domain have much higher affinity (about 9 orders of magnitude) than natural thiols such as glutathione or cysteine and nonphysiological thiols such as 2-mercaptoethanol [Zeng et al. (1998) supra]. The wild-type MerR protein binds mercuric ion with an affinity of $10^{-9}$ M even in the presence of millimolar quantities of thiols.

Figure 2:
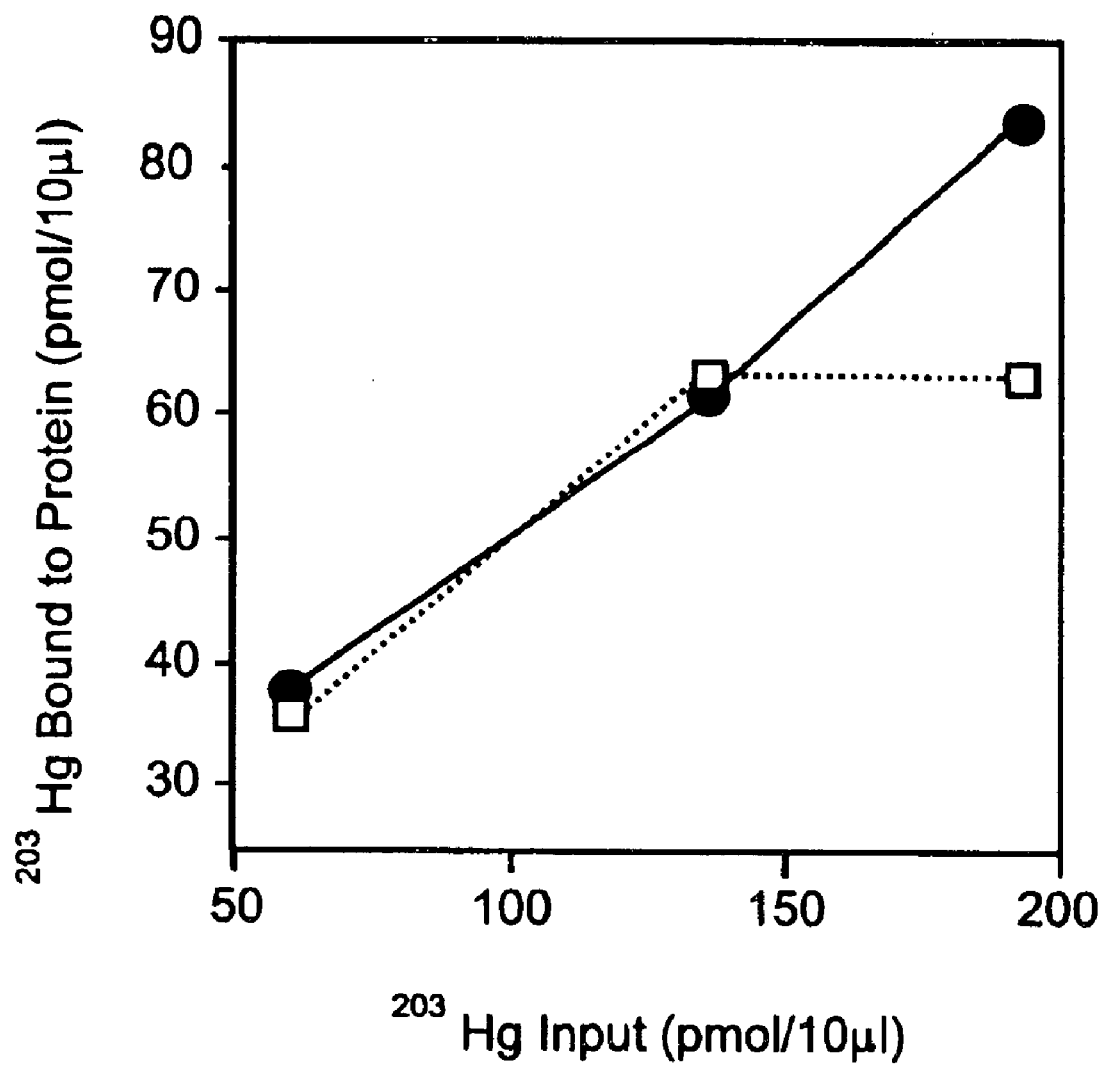
FIG. 2 graphically illustrates the results of Hg(II) binding as measured by equilibrium ultrafiltration. The capacity of the chelon appears to be higher than that of the naturally occurring MerR protein.
Figure 3:
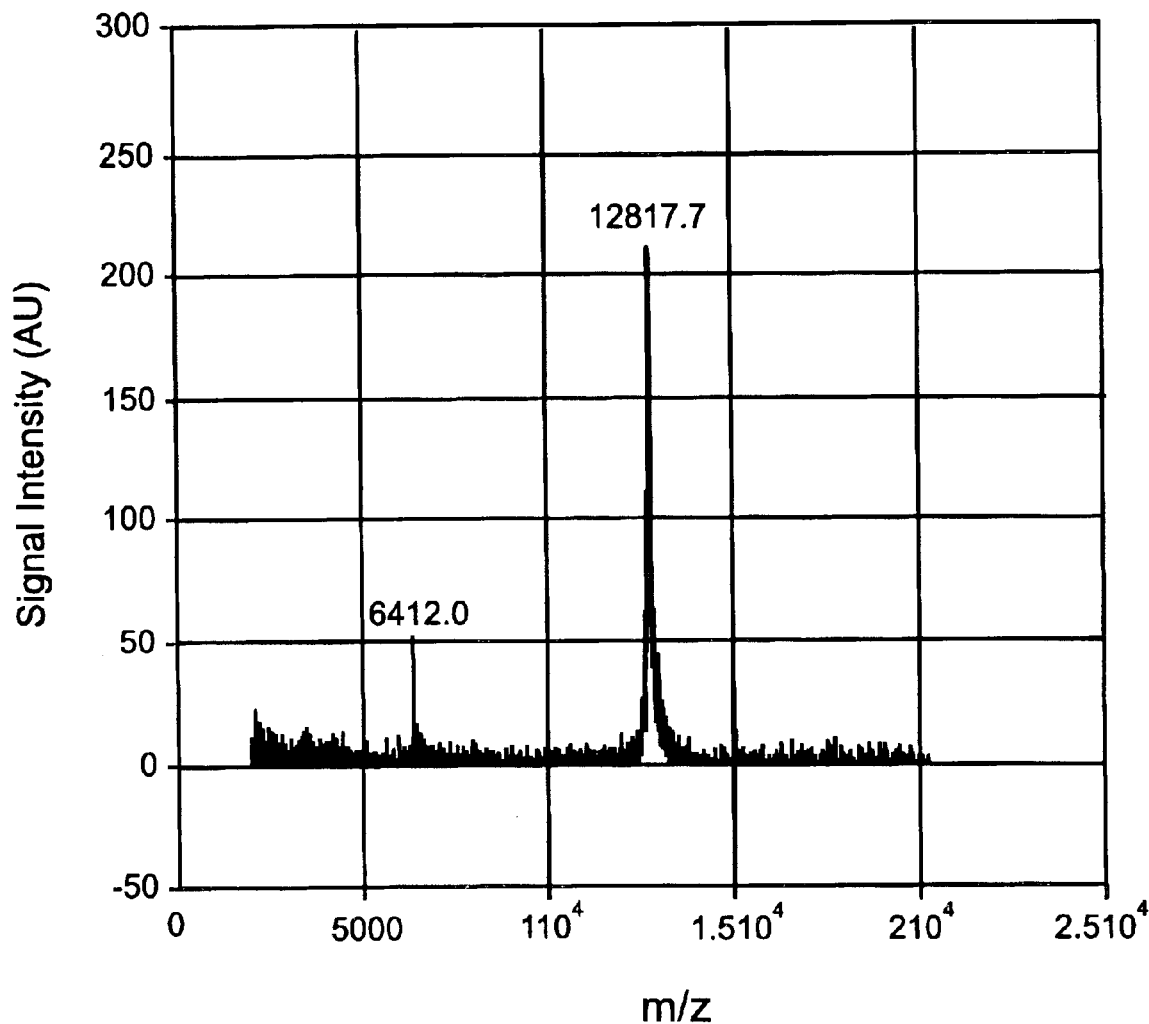
FIG. 3 provides the results of Matrix Assisted Laser Desorption Ionization Time of Flight (MALDI-TOF, using a Bruker Reflex Instrument) of a purified mercury-specific chelon protein as eluted from a StrepTag column. Peaks shown are the single positive charge at 12,817.7 Da and the double positively charged species at 6412.0 Da. Both peaks are in reasonable agreement with the expected values for the chelon protein (12821.58 Da). Tailing on major peaks arises from random adducts of sinapinic acid from the matrix (224 Da).

In the chelons of the present invention, the metal binding site requires that an antiparallel association of sequence motifs come together in a way that mimics the natural mercuric ion binding site of MerR dimers. The ability to bind metal ions by the chelon is documented in FIG. 2.

Figure 5:
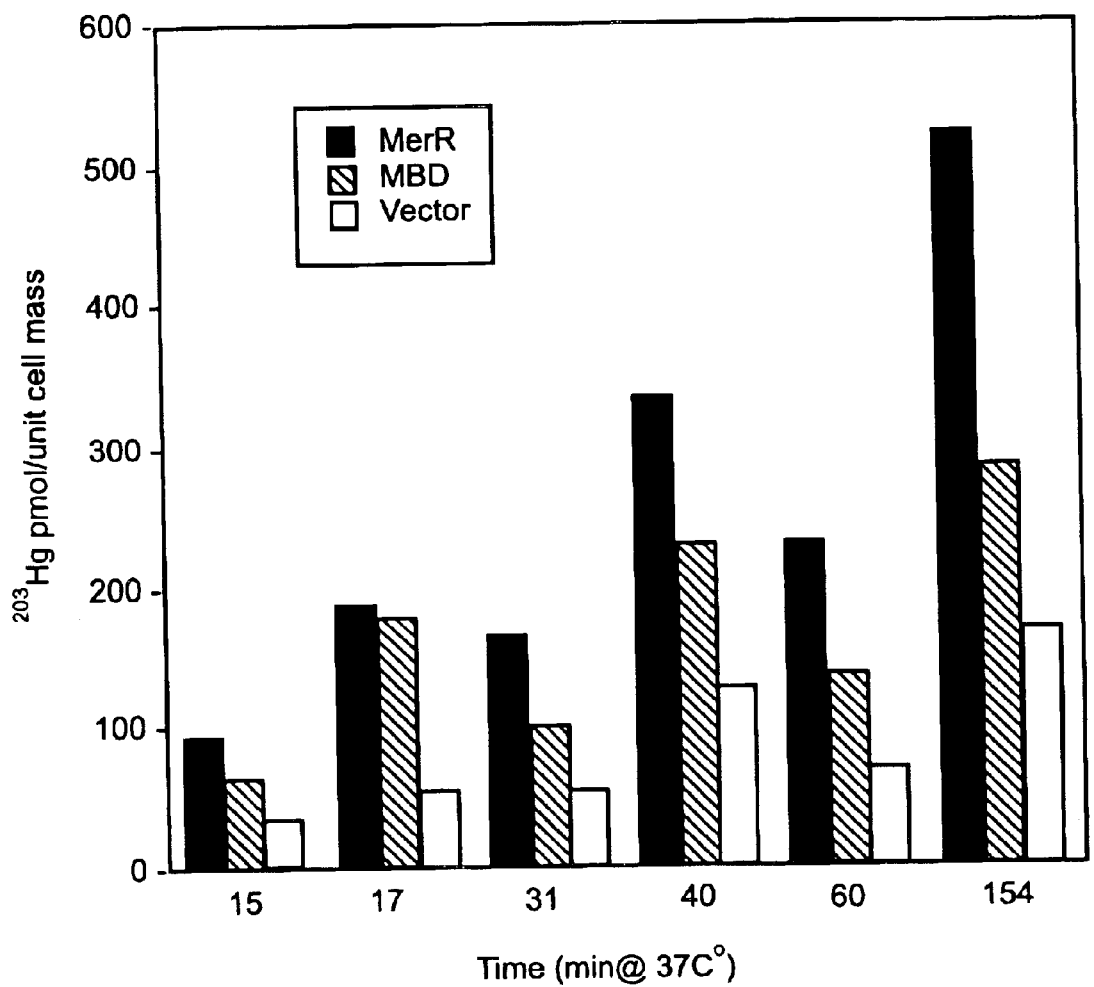
FIG. 5 shows binding of $^{203}$Hg ions by cells expressing MerR or chelon protein (SEQ ID NO:2); the data were collected in two experiments.

Bacterial cells over-expressing a chelon (MBD) or MerR protein intracellularly bind more Hg than a strain carrying only the plasmid vector (FIG. 5). Western analysis indicates that the MerR and chelon proteins are produced in similar amounts. However, MerR binds Hg ions somewhat better than does the chelon protein. Without wishing to be bound by any particular theory, it is believed that this may arise because of differences in folding stability for the very short, artificial chelon compared to the full-length MerR protein inside the cell. Nonetheless, chelon protein expression clearly increases the amount of Hg bound.

When the chelon and MerR proteins are each attached to a solid substrate (Streptactin Sepharose) in vitro via StrepTag streptavidin/Streptactin sequences (Genosys) both bind the solid substrate with equal efficiency, i.e. with very similar affinity (in terms of motes of protein bound to the resin), but the bound chelon is more effective than bound MerR protein in binding Hg ions (Table 3). Although the Hg occupancy of the chelon is only 50%, its proficiency in this regard compared to MerR (which binds Hg with ca. 3-fold less efficiency) is expected because each tethered copy of the chelon contains a complete Hg binding site. However, for MerR, the tethered monomer must either capture a free monomer from solution or must contact a monomer bound to an adjacent site on the substrate surface in order to form the dimeric Hg binding site. Without wishing to be bound by theory, we believe that this "search" process limits the efficiency of tethered full length MerR as compared to the single polypeptide chelon in capturing Hg.

The chelons of the present invention bind a variety of transition metals with relatively high efficiency (affinity). In these experiments we exposed fully reduced chelon (SEQ ID NO: 4) to a 2-fold molar excess of the indicated metals in the presence of a large excess of competing thiol (5 mM 2-mercaptoethanol) and then dialyzed the reactions extensively against a buffered thiol and determined the metal content by inductively coupled plasma-mass spectrometry (ICP-MS). The MBD binds cadmium, cobalt, copper, lead, nickel, and zinc with an affinity equivalent to that for Hg(II), i.e. one metal atom per protein molecule. Interestingly, it does not bind two other "thiophilic metals" iron and arsenite, A(III).

The natural MerR protein has an additional property of interest: it undergoes a conformation (allosteric) change when metal ion binds to it [Heltzel et al. (1990) Biochemistry 29, 9572–9584]. In the intact protein this change is transduced from the metal binding domain to the DNA binding domain and results in underwinding of the DNA to foster transcription initiation. The MerR binding domain is the first functional metalloprotein subdomain which is sufficiently small and stable for use outside of the cellular environment [Zeng et al. (1998) supra].

The present inventors discovered that the chelon protein of SEQ ID NO:4 binds the same ions as the wild-type MerR protein. While the wild type MerR protein binds certain ions other than mercuric ions, those other ions do not induce transcription of the mer operon in vivo or in vitro.

Because most proteins require that all of their subdomains fold together with each other in order to achieve a stable tertiary structure and avoid degradation, it was not obvious that any single subdomain of MerR could be produced as a stable functional subdomain within the cells. The present findings indicate that the tendency of the MerR metal binding domain to fold into stable, functional polypeptide structure is strong. It was also not obvious that the unnatural direct linkage of two of these domains would yield a stable protein, much less one which retained the metal binding properties of the natural MerR dimer.

Building both halves of the metal binding domain into a single polypeptide eliminates the problem of achieving sufficiently high protein concentrations assure the optimum formation of dimers; i.e., the two halves of the binding domain don't need to "find" each other because they are covalently joined by a linker peptide region. Even with an affinity tag the chelon derivative is only slightly larger than a typical metallothionein and it will be much less costly to the cell to produce than the full length MerR protein. The stability of the folded form of the metal binding domain and the allosteric change which the MerR metal binding domain undergoes allow its use outside the cell in both metal detection and metal sequestration strategies.

In metal sequestration application of the present chelon technology, the cells in which the chelon is expressed contain strongly bound metal ions which will not significantly exchange with extracellular metal ions. Due to the high affinity binding, those cells are significantly more resistant to the heavy metal ions than comparison cells which do not express the chelon protein(s). Bacterial cells engineered to express at least one chelon coding sequence are useful in bioremediation of contamination sites. Colonizing the intestinal tract with nonpathogenic nontoxigenic bacteria engineered to express at least one chelon reduces enterohepatic recycling of mercury and makes elimination more rapid and more efficient. Most of the ingested and inhaled mercury is processed through the intestinal tract of primates, and colonization with chelon-producing microbes reduces uptake of heavy metal ions into circulation.

Purified chelon proteins can be used isolated away from the cellular environment. Present water treatment resins have relatively low affinities for toxic metals when nontoxic metal are in comparatively high concentration and compete for binding to the resin. A resin which "ignores" nontoxic metals and binds only a target metal of interest (especially mercury or cadmium cations) can augment existing water treatment regiments. Immobilizing a chelon of the present invention to a solid support allows for the design of water treatment resins useful in removing mercury and/or cadmium, depending on the choice of the particular chelon or a combination of chelons. Suitable solid supports include, without limitation, latex particles, glass beads, hydrogels, polystyrene and liposomes. The particles or beads can be fabricated from a variety of materials and can have any shape, including a spherical shape. The chelon(s) can be on the surfaces of the beads or particles, or they can be within porous beads or particles. The beads can have added surface groups to act as spacers to improve access to the metal ion binding sites of the attached chelon proteins or to facilitate attachment of the chelon molecules, for example carboxyl groups on latex or amino modifications on polystyrene. Polymers with free amino groups that are useful in conjunction with gelling agents include, without limitation, alginate amine, chitosan, pectin, and polyethylene imine. Additionally, affixing the chelon(s) to microspheres with selective permeability allows it to access mercury attached to low molecular weight thiols in the environment while protecting the chelon protein from degradative enzymes in the environment. Magnetic versions of such microspheres can be disseminated in the soil. After a time sufficient to allow the microspheres to become saturated with toxic metal ions, the beads are recovered via standard magnetic recovery techniques.

MerR or chelon proteins can be readily engineered to facilitate purification and/or immobilization to a solid support of choice. For example, a stretch of 6–8 histidines can be engineered through mutagenic polymerase chain reaction or other recombinant DNA technology to allow purification of expressed recombinant protein over an nitrilotriacetic acid (NTA) column using commercially available materials. Other oligopeptide "tags" which can be fused to a protein of interest by such techniques include, without limitation, strep-tag (Sigma-Genosys, The Woodlands, Tex.) which directs binding to streptavidin or its derivative streptactin (Sigma-Genosys); a calmodulin-binding peptide fusion system which allows purification using a calmodulin resin (Stratagene, La Jolla, Calif.); a maltose binding protein fusion system allowing binding to an amylose resin (New England Biolabs, Beverly, Mass.); and an oligo-histidine fusion peptide system which allows purification using a $Ni^{2+}$-NTA column (Qiagen, Valencia, Calif.).

The range over which the chelons of the present invention act to bind mercury (and cadmium in the case of the mercury and cadmium specific chelon) extend from as low as $10^{-9}$ M and up to about 1 M. Binding of mercury and cadmium ions is effective over the pH range from 5 to 9, desirably from 6 to 8.5, and more preferably from 7 to 8.

Various techniques can be used to immobilize the chelon proteins on the surfaces of a solid support, provided that metal ion binding is not impaired due to the technique used for protein immobilization. The protein can be coated on the surface of the beads and/or interior surfaces of porous beads can similarly be coated. Chelon protein can be mixed with liquid phase material prior to gelling and bead formation. In a specifically exemplified embodiment, either chelon or MerR protein is linked to Streptactin Sepharose.

With poisoning with mercury, the enterohepatic recycling of mercury slows its elimination from the body. Since colonization of humans with a recombinant strain of bacteria is likely to face regulatory hurdles, an alternative strategy is the use of microspheres to which the chelon is covalently bound. Mounting the chelon protein in a microsphere with pores sufficiently large to allow diffusion of a low molecular weight thiols but sufficiently small to block diffusion of digestive proteases produces a robust high affinity and high specificity nonabsorbable sequestering agent. These microspheres pass readily through the intestinal tract, collecting mercury on the way to elimination via natural processes. An advantage of the chelon-containing microspheres of the present invention over prior art sulfonated amberlite resins is the increased specificity for the toxic metal over that of other divalent cations, such as copper or zinc, whose depletion would be deleterious to the human or animal host.

It is well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

The complete nucleotide sequence encoding the MerR protein of Tn21 is available on GenBank, Accession No.

Figure 4:
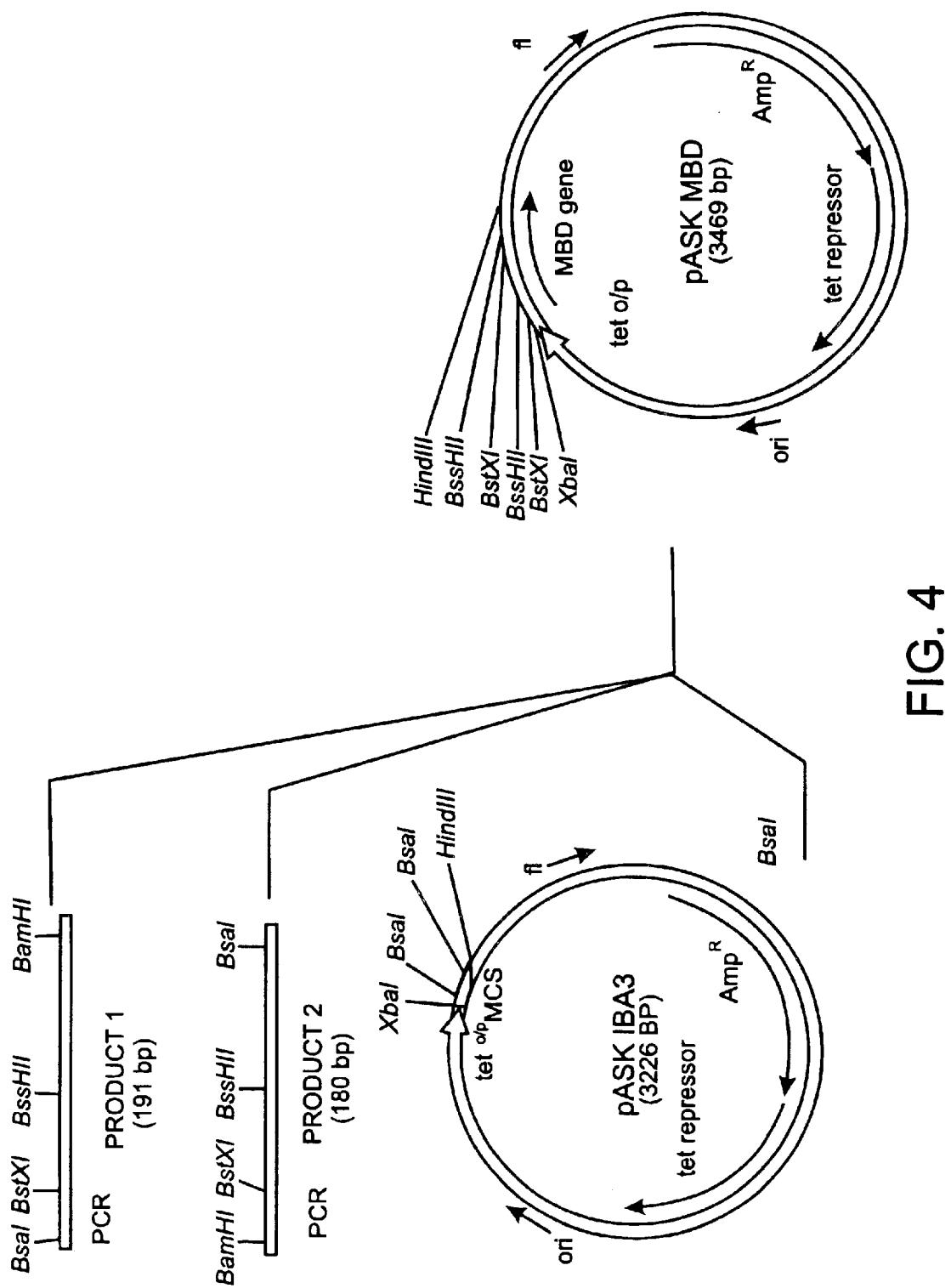
FIG. 4 summarized steps in the cloning of the chelon coding sequence into the pASK-IBA3 vector. In PCR reaction 1 (with primers corresponding to SEQ ID NO:13 and SEQ ID NO:14) and PCR reaction 2 (with primers corresponding to SEQ ID NO:15 and SEQ ID NO:16), each with pNH9 as template, the chelon coding sequence DNA fragment was synthesized. The two PCR products were digested with BsaI and BamHI and ligated into pASK IBA3 (Genosys) which had been cut with BsaI. The ligation products were transformed into *Escherichia coli* XL1-Blue and transformants were selected using ampicillin. In the resulting recombinant vector (pASK MBD, carrying the chelon of SEQ ID NO:4), chelon expression is induced by anhydrotetracycline. Tetracycline can also be used to induce expression. PNH9 has been described in Hamlett et al. (1992) *J. Bacteriol.* 174:6377–6385.

P07044. Plasmid pASK-IBA3 is commercially available from Sigma-Genosys (The Woodlands, Tex.). The StrepTagII (trademark of Institut fur Bioanalytik GmbH) technology (which depends on streptavidin binding by particular residues, i.e., WSHPQFEK amino acid residues present at the C-terminus of the recombinant chelon protein; amino acids 110–117 of SEQ ID NO:4) is described in U.S. Pat. No. 5,506,121, incorporated by reference herein. The recombinant mercury-binding chelon expression plasmid is constructed by joining PCR amplicands of two copies of sequences encoding the metal binding domain (residues 81–127) of MerR. To facilitate joining of these 2 metal binding domains coding sequences in a direct tandem repeat, the primers used in the amplification are designed to have a common BamHI restriction endonuclease recognition site to allow the to be joined and also to include a linker regions between them (See FIG. 4). The outer primers add a BsaI site to each end, allowing the entire chelon coding sequence to be cloned into the vector pASK-IBA3 (at the BsaI site remaining after the short BsaI fragment is removed and both BsaI fragments were eliminated). The expression of the tagged protein is under the control of the tetracycline-inducible tertA promoter, and the polylinker into which a coding sequence of interest is cloned contains restriction endonuclease recognition sites for BsaI and BsmFI. Crude extracts of the recombinant *E. coli* cells containing the tagged chelon protein are treated to purify the tagged protein in accordance with instructions from the manufacturer.

Alternatively, controlled expression of the chelon can be achieved by inserting the coding sequence into pBAD (Invitrogen, Carlsbad, Calif.) for expression induced by arabinose.

The nucleotide sequence encoding the chelon protein in given in Table 1B. It is inserted into the vector for tetracycline-regulated synthesis at a BsaI restriction site.

For mercury ion-regulated expression of the chelon coding sequence, the chelon coding sequence is cloned using pCC306 [Condee and Summers (1992) *J. Bacteriol.* 174:8094–8101]. The luciferase coding sequences are replaced with the chelon coding sequence. Chelon expression is regulated by mercury in conjunction with the naturally occurring MerR protein. There is no need for a tag to assist in purification because recombinant host cells with the mercury-regulated chelon expression plasmid are to be used without protein purification, at least in certain applications. This vector is based on the p15A replicon, and it is suitable for use in all Enterobacteriaceae. Such recombinant enteric bacteria (which are nontoxigenic and nonpathogenic) are suitable for use in the in vivo sequestration and elimination of mercuric ion from the human or animal gastrointestinal tract.

Techniques and agents for introducing and selecting for the presence of heterologous DNA, i.e., a chelon coding sequences operably linked to transcription and translation regulatory sequences functional in plant cells. in plant cells and/or tissue are well-known. Constitutive transcription regulatory sequences include the Cauliflower Mosaic Virus 35S and 19S promoters, and sequences which provide for efficient translational expression are described in, e.g., U.S. Pat. No. 5,668,294 (Meagher et al.) And U.S. Pat. No. 5,874,242 (Mensa-Wilmot). Where expression is preferred in above the ground plant parts, a rubisco promoter, for example, from soybean, can be used to drive chelon expression. The soybean rubisco promoter sequence is available from GenBank as Accession No. X58684. Genetic markers allowing for the selection of heterologous DNA in plant cells are readily available, e.g., genes carrying resistance to an antibiotic such as kanamycin, hygromycin, gentamycin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology*, A. Weissbach and H. Weissbach, eds., Academic Press, Inc., San Diego, Calif. (1988).

Techniques for genetically engineering plant cells and/or tissue with an expression cassette comprising a constitutive promoter or an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamycin, or bleomycin.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella (1983), Bevan (1983), Klee (1985) and EPO publication 120,516 (Schilperoort et al.). In addition to plant transformation vectors derived from the Ti or root-inducing (Ri) plasmids of Agrobacterium, alternative methods can be used to insert the DNA constructs of this invention into plant cells.

The choice of vector in which the DNA of interest is operatively linked depends directly, as is well known in the art, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia Biotech (Uppsala, Sweden), and pBLUESCRIPT and pBS available from Stratagene (La Jolla, Calif.). A vector of the present invention may also be a Lambda phage vector including those Lambda vectors described in *Molecular Cloning: A Laboratory Manual, Second Edition*, Maniatis et al., eds., Cold Spring Harbor Press (1989) and the Lambda ZAP vectors available from Stratagene (La Jolla, Calif.). Other exemplary vectors include pCMU [Nilsson et al. (1989) *Cell* 58:707]. Other appropriate vectors may also be synthesized, according to known methods; for example, vectors pCMU/K$^b$ and pCMUII used in various applications herein are modifications of pCMUIV (Nilson et al., supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) *Meth. in Enzymol.* 153:253–277, and several other expression vector systems known to function in plants. See for example, Verma et al., No. WO87/00551; Cocking and Davey (1987) *Science* 236:1259–1262.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Science* 244:1293; Leemans (1993) *Bio/Technology.* 11:522; Beck et al. (1993) *Bio/Technology.* 11:1524; Koziel et al. (1993) *Bio/Technology.* 11:194; and Vasil et al. (1993) *Bio/Technology.* 11:1533). Techniques are well-known to the art for the introduction of DNA into monocots as well as dicots, as are the techniques for culturing such plant tissues and regenerating those tissues.

For use in pseudomonads and many other Gram negative bacteria, IncQ or IncP vectors are particularly appropriate, and a large variety of such vectors are known in the art. For use in Gram positive bacteria any of a number of vectors maintained and replicated in particular organisms of interest, especially *Bacillus subtilis* and other species, are well known and readily available to the art. See, e.g., Pouwels, P. H. et al. (eds.) *Cloning Vectors*, Elsevier, Amsterdam, NL. Vectors suitable for use in filamentous fungi such as Aspergillus and Trichoderma are known as are vectors for use in yeasts including *Saccharomyces cerevisiae* and *Pichia pastoris*. The merOP regulatory region and the MerR coding sequence are desirably inserted into the vector of choice according to the desired host cell so that MerR or chelon expression is turned on only in the presence of mercury.

Polyclonal and/or monoclonal antibodies capable of specifically binding to a chelon of the present invention are provided. The term antibody is used to refer both to a homogenous molecular entity, or a mixture such as a serum product made up of a plurality of different molecular entities. Monoclonal or polyclonal antibodies specifically reacting with a chelon of the present invention can be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York. Also, recombinant immunoglobulins may be produced by methods known in the art, including but not limited to, the methods described in U.S. Pat. No. 4,816,567. Monoclonal antibodies with affinities of $10^8$ M$^{-1}$, preferably $10^9$ to $10^{10}$ or more are preferred.

Antibodies specific for the artificial metal binding proteins (chelons) of the present invention are useful, for example, as probes for assessing expression, for determining amounts of artificial binding proteins in free or bound form or for detecting the presence of the artificial metal binding proteins of the present invention in a test sample. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States patents describing the use of such labels include, but are not limited to, U.S. Pat. Nos. 3,817,837; 3,850,752; 3,939,350; 3,996, 345; 4,277,437; 4,275,149; and 4,366,241.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218: Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) DNA Cloning Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

Each reference cited in the present application is incorporated by reference herein to the extent that it is not inconsistent with the present Specification.

The description provided herein is for illustrative purposes, and is not intended to limit the scope of the invention as claimed herein. Any variations in the exemplified articles and/or methods which occur to the skilled artisan are intended to fall within the scope of the present invention.

TABLE 1A

Amino acid sequence of wild-type MerR protein from Tn21

(SEQ ID NO:2)
MENNLENLTIGVFAKAAGVNVETIRFYQRKGLLREPDKPYGSIRRYGEAD

VVRVKFVKSAQRLGFSLDEIAELLRLDDGTHCEEASSLAEHKLKDVREKM

ADLARMETVLSELVCACHARKGNVSCPLIASLQGEAGLARSAMP

TABLE 1B

Nucleotide sequence encoding the wild-type MerR protein from Tn21

(SEQ ID NO:1)

```
  1 ATGGAAAATA ATTTGGAAAA CCTGACCATT GGCGTTTTTG
                                     CCAAGGCGGC
 51 CGGGGTCAAC GTGGAGACAA TCCGCTTCTA TCAGCGCAAG
                                     GGCCTGTTGC
101 GGGAACCGGA CAAGCCTTAC GGCAGCATCC GCCGCTATGG
                                     GGAGGCGCAC
151 GTGGTTCGGG TGAAATTCGT GAAATCGGCA CAGCGGCTGG
                                     GGTTCAGTCT
201 GGACGAGATT GCCGAGCTGT TGCGGCTCGA CGATGGCACC
                                     CACTGCGAGG
251 AGGCCAGCAG CCTGGCCGAA CACAAGCTCA AGGACGTGCG
                                     CGAGAAGATG
301 GCCGACTTGG CGCGCATGGA AACCGTGCTG TCTGAACTCG
                                     TGTGCGCCTG
351 CCATGCACGA AAGGGGAATG TTTCCTGCCC GTTGATCGCG
                                     TCACTACAGG
401 GCGAAGCAGG CCTGGCAAGG TCAGCTATGC CTTAG
```

TABLE 1C

Complete amino acid sequence of the chelon protein (SEQ ID NO:4) showing novel residues not found in wild-type MerR. The last underlined residues are derived from the StrepTag vector (Genosys) and are not essential to the metal-binding domain nor do they interfere with metal binding. These residues are only important for purification of the protein

MTHCEEASSLAEHKLKDVREKMADLARMETVLSELVCACHARKGNVSCPL

IASLQGSSGTHCEEASSLAEHKLKDVREKMADLARMETVLSELVCACHAR

KGNVSCPSAWSHPQFEK

TABLE 1D

Complete 321 nucleotide DNA sequence encoding the essential 107 residues of the Chelon protein (SEQ ID NO:3). This DNA sequence does not include the sequence encoding the StrepTag portion of the protein. The DNA sequence for the StrepTag is incorporated in the Sigma-Genosys vector. Any other affinity tag or none at all (i.e. the normal wild-type sequence of the protein) could be incorporated for use in alternative protein purification schemes.

ATGACACACTGCGAGGAGGCCAGCAGCCTGGCCCAACACAAGCTCAAGGA

CGTGCGCGAGAAGATGGCCGACTTGGCGCGCATGGAAACCGTGCTGTCTG

AACTCGTGTGCGCCTGCCATGCACGAAAGGGGAATGTTTCCTGCCCGTTG

ATCGCGTCACTACAGGGATCCTCAGGCACCCACTGCGAGGAGGCCAGCAG

CCTGGCCGAACACAAGCTCAAGGACGTGCGCGAGAAGATGGCCGACTTGG

CGCGCATGGAAACCGTGCTGTCTGAACTCGTGTGCGCCTGCCATGCACGA

AAGGGGAATGTTTCCTGCCCG

TABLE 2

Amino acid sequences of chelons which bind cadmium as well as mercury ions with high affinity. The residues which differ from the mercury specific chelon (see Table 1B) are shown with bold and underlining.

(SEQ ID NO:5)
MTHCEEVSSLAEHKLKDVREKMADLARMETVLSELVCACHARKGNVSCPL
IASLQGSSGTHCEEVSSLAEHKLKDVREKMADLARMETVLSELVCACHAR
KGNVSCPSAWSHPQFEK (SEQ ID NO:6)
MTHCEEASSLVEHKLKDVREKTMADLARMETVLSELVCACHARKGNVSCP
LIASLQGSSGTHCEEASSLVEHKLKDVREKMADLARMETVLSELVCACHA
RKGNVSCPSAWSHPQFEK (SEQ ID NO:7)
MTHCEEASSLAEHKLKDVRETMADLARMETVLSELVCACHARKGNVSC
PLIASLQGSSGTHCEEASSLAEHKLKDVRETMADLARMETVLSELVCACH
RKGNVSCPSAWSHPQFEK (SEQ ID NO:8)
MTHCEEAS SLAEHKLKDVREQMADLARMETVLSELVCACHARKGNVSCP
LIASLQGSSGTHCEEASSLAEHKLKDVREQMADLARMETVLSELVCACHA
RKGNVSCPSAWSHPQFEK (SEQ ID NO:9)
MTHCEEASSLAEHKLKDVREKMADLARVETVLSELVCACHARKGNVSCPL
IASLQGSSGTHCEEASSLAEHKLKDVREKMADLARVETVLSELVCACHAR
KGNVSCPSAWSHPQFEK (SEQ ID NO:10)
MTHCEEASSLAEHKLKDVREKMADLARIETVLSELVCACHARKGNVSCPL
IASLQGSSGTHCEEASSLAEHKLKDVREKMADLARIETVLSELVCACHAR
KGNVSCPSAWSHPQFEK (SEQ ID NO:11)
MTHCEEASSLAEHKLKDVREKMADLARMETVLSELVCACHARKGNVPCPL
IASLQGSSGTHCEEASSLAEHKLKDVREKMADLARMETVLSELVCACHAR
KGNVPCPSAWSHPQFEK (SEQ ID NO:12)
MTHCEEASSLAEHKLKDVREKMADLARMETVLSELVCACHARKGNVSCPL
IALLQGSSGTHCEEASSLAEHKLKDVREKMADLARMETVLSELVCACHAR
KGNVSCPSAWSHPQFEK

TABLE 3

Hg-binding by Resin-tethered MerR and Chelon (SEQ ID NO:4)

| Protein | moles Hg bound/mole protein |
| --- | --- |
| chelon | 0.490 |
| MerR | 0.194 |

TABLE 4

Metal Binding by Chelon (SEQ ID NO:4)

| Metal | moles bound/mole protein |
| --- | --- |
| arsenic | below limit of detection |
| cadmium | 0.66 |
| cobalt | 0.79 |
| copper | 0.95 |
| iron | below limit of detection |
| lead | 0.93 |
| nickel | 0.75 |
| zinc | 0.38 |

TABLE 5A

Primers for construction of pASK-MBD:

Product 1:

(SEQ ID NO:13)
Forward: 5' TGCGGCGGTCTCAAATGACACACTGCGAGGAGG 3'

(SEQ ID NO:14)
Reverse: 5' GCCTGAGGATCCCTGTAGTGACGCGATCAACGG 3'

Product 2:

(SEQ ID NO:15)
Forward: 5' CTACAGGGATCCTCAGGCACCCACTGCGAG 3'

(SEQ ID NO:16)
Reverse: 5' CTGTAGGGTCTCGGCGCTCGGGCAGGAAACATT 3'

TABLE 5B

Sequence of pASK-MBD gen

(SEQ ID NO:17)
ATGACACACTGCGAGGAGGCCAGCAGCCTGGCCGAACACAAGCTCAAGGA

CGTGCGCGAGAAGATGGCCGACTTGGCGCGCATGGAAACCGTGCTGTCTG

AACTCGTGTGCGCCTGCCATGCACGAAAGGGGAATGTTTCCTGCCCGTTG

ATCGCGTCACTACAGGGATCCTCAGGCACCCACTGCGAGGAGGCCAGCAG

CCTGGCCGAACACAAGCTCAAGGACGTGCGCGAGAAGATGGCCGACTTGG

CGCGCATGGAAACCGTGCTGTCTGAACTCGTGTGCGCCTGCCATGCACGA

AAGGGGAATGTTTCCTGCCCGAGCGCTTGGAGCCACCCGCAGTTCGAAAA

ATAA

TABLE 5C

Adjacent plasmid regions with enzyme cutting sites labeled

(SEQ ID NO:18)
CCATCGAATGGCCAGATGATTAATTCCTAATTTTTGTTGACACTCTATCA

TABLE 5C-continued

Adjacent plasmid regions with enzyme cutting sites labeled

TTGATAGAGTTATTTTTACCACTCCCTATCAGTGATAGAGAAAAGTGAAAT

XbaI
GAATAGTTCGACAAAAATCTAGATAACGAGGGCAAAAAATGACACACTGC
▸MetThrHisCys

BstXI
GAGGAGGCCAGCAGCCTGGCCGAACACAAGCTCAAGGACGTGCGCGAGAA
GluGluAlaSerSerLeuAlaGluHisLysLeuLysAspValArgGluLy

BssHII
GATGGCCGACTTGGCGCGCATGGAAACCGTGCTGTCTGAACTCGTGTGCG
sMet▸AlaAspLeuAlaArgMetGluThrValLeuSerGluLeuValCysA

CCTGCCATGCACGAAAGGGGAATGTTTCCTGCCCGTTGATCGCGTCACTA
laCysHisAlaArgLysGlyAsnValSerCysProLeuIleAlaSerLeu

BstXI
CAGGGATCCTCAGGCACCCACTGCGAGGAGGCCAGCAGCCTGGCCGAACA
GlnGly▸SerSerGlyThrHisCysGluGluAlaSerSerLeuAlaGluHi

BssHII
CAAGCTCAAGGACGTGCGCGAGAAGATGGCCGACTTGGCGCGCATGGAAA
sLysLeuLysAspValArgGluLysMetAlaAspLeuAlaArgMetGluT

CCGTGCTGTCTGAACTCGTGTGCGCCTGCCATGCACGAAAGGGGAATGTT
hrValLeu▸SerGluLeuValCysAlaCysHisAlaArgLysGlyAsnVal

TCCTGCCCGAGCGCTTGGAGCCACCCGCAGTTCGAAAAATAAT
SerCysProSerAlaTrpSerHisProGlnPheGluLys

HindII
AAGCTTGACCTGTGAAG

\*\*
Lighter print: Chelon coding region; followed in regular print by sequence encoding 10-amino acid-tail (Strep-tagII) at the C terminus of the MBD.

---

What is claimed is:

1. A non-naturally occurring recombinant DNA molecule comprising a nucleotide sequence encoding a chelon protein which binds mercuric and cadmium ions, wherein the chelon protein comprises an amino acid sequence selected from the group consisting of amino acids 1 to 107 of SEQ ID NO:4 amino acids 1 to 107 of SEQ ID NO:5, amino acids 1 to 108 of SEQ ID NO:6 amino acids 1 to 107 of SEQ ID NO:7, amino acids 1 to 107 of SEQ ID NO:8, amino acids 1 to 107 of SEQ ID NO:9: amino acids 1 to 107 of SEQ ID NO:10: amino acids 1 to 107 of SEQ ID NO:11: and amino acids 1 to 107 of SEQ ID NO:12.

2. A host cell transformed with the recombinant DNA molecule of claim 1.

3. The non-naturally occurring recombinant DNA molecule of claim 1 wherein the nucleotide sequence encodes a chelon protein having the amino acid sequence given in amino acids 1 to 107 of SEQ ID NO:4.

4. The non-naturally occurring recombinant DNA molecule of claim 3, wherein the nucleotide sequence comprises SEQ ID NO: 3.

5. A host cell transformed with the recombinant DNA molecule of claim 4.

6. The transformed host cell of claim 5, wherein the chelon protein comprises the amino sequence given in amino acids 1 to 107 of SEQ ID NO:4.

7. A method for recombinantly producing a chelon protein in a host cell, said method comprising the steps of:
   a) transforming a host cell with a vector comprising a promoter active in said host cell operably linked to nucleotide sequence encoding a chelon protein, wherein said chelon protein comprises an amino acid sequence selected from the group consisting of amino acids 1 to 107 of SEQ ID NO:4, amino acids 1 to 107 of SEQ ID NO:5, amino acids 1 to 108 of SEQ ID NO:6, amino acids 1 to 107 of SEQ ID NO:7, amino acids 1 to 107 of SEQ ID NO:8, amino acids 1 to 107 of SEQ ID NO:9, amino acids 1 to 107 of SEQ ID NO:10, amino acids 1 to 107 of SEQ ID NO:11, amino acids 1 to 107 of SEQ ID NO:12 to produce a recombinant host cell; and
   b) culturing the recombinant host cell under conditions wherein said chelon protein is expressed.

* * * * *

UNITED STATES PATENT AND TRADEMARK OFFICE
CERTIFICATE OF CORRECTION

PATENT NO.    : 6,750,042 B2
DATED         : June 15, 2004
INVENTOR(S)   : Summers et al.

It is certified that error appears in the above-identified patent and that said Letters Patent is hereby corrected as shown below:

Title page,
Item [56], References Cited, OTHER PUBLICATIONS, insert the following references:
-- "Selifonova, O. et al.," references, "Bioluminescent Sensors for Detection of Bioavailable Hg(II) in the Environment" (Sept. 1993) Applied and Environmental Microbiology 59(9):3083-3090.
  "Shewchuk, L.M. et al.," references, "Transcriptional Switching by the MerR Protein: Activation and Repression Mutants Implicate Distinct DNA and Mercury(II) Binding Domains" (1989) Biochemistry 28(5): 2340-2344.
  "Shewchuk, L.M. et al.," references, "Transcriptional Switching by the Metalloregulatory MerR Protein: Initial Characterization of DNA and Mercury(II) Binding Activities" (1989) Biochemistry 28(5):2331-2339.
  "Steele, R.A., and Opella, S.J.," references, "Structures of the Reduced and Mercury-Bound Forms of MerP, the Periplasmic Protein from the Bacterial Mercury Detoxification System" (1997) Biochemistry 36(23):6885-6895.
  "Summers, A.O.," references, "Untwist and Shout: a Heavy Metal-Responsive Transcriptional Regulator" (May 1992) J. Bacteriol. 174(10):3097-3101.
  "Utschig, L.M. et al.," references, "Mercury-199 NMR of the Metal Receptor Site in MerR and its Protein-DNA Complex" (April 1995) Science 268:380-385.
  "Utschig, L.M. et al.," references, "Biochemical and Spectroscopic Probes of Mercury(II) Coordination Environments in Proteins" (1993) Methods Enzymol. 226:71-97.
  "Veglia, G. et al.," references, "The Structure of the Metal-Binding Motif GMTCAAC Is Similar in an 18-Residue Linear Peptide and the Mercury Binding Protein MerP" (March 2000) J. Am. Chem. Soc. 122(10):2389-2390.
  "Wright, J.G. et al.," references, "Coordination Chemistry of the Hg-MerR Metalloregulatory Protein: Evidence for a Novel Tridentate Hg-Cysteine Receptor Site" (1990) J. Am. Chem. Soc. 112:2434-2435.
  "Zeng, Q. et al.," references, "The Core Metal-Recognition Domain of MerR" (1998) Biochemistry 37(45):15885-15895.

UNITED STATES PATENT AND TRADEMARK OFFICE
CERTIFICATE OF CORRECTION

PATENT NO. : 6,750,042 B2
DATED : June 15, 2004
INVENTOR(S) : Summers et al.

It is certified that error appears in the above-identified patent and that said Letters Patent is hereby corrected as shown below:

OTHER PUBLICATIONS, (cont'd),
 "Kulkarni, R.D. and Summers, A.O.," references, "MerR Cross-Links to the $\alpha,\beta$, and $\sigma^{70}$ Subunits of RNA Polymerase in the Preinitiation Complex at the *mer* TPCAD Promoter" (March 1999) Biochemistry 38(11):3362-3368. --

Signed and Sealed this

Twenty-fifth Day of January, 2005

JON W. DUDAS
*Director of the United States Patent and Trademark Office*